United States Patent [19]

Obendorf et al.

[11] 4,152,526

[45] May 1, 1979

[54] N-ACYL DERIVATIVES OF 3-AMINO-2,4,6-TRIIODOBENZOIC ACID

[75] Inventors: Werner Obendorf; Ernst Schwarzinger, both of Linz, Austria

[73] Assignee: Chemie Linz Aktiengesellschaft, Austria

[21] Appl. No.: 829,467

[22] Filed: Aug. 31, 1977

[51] Int. Cl.² .................. C07C 101/447; A61K 29/02
[52] U.S. Cl. ........................................ 562/455; 424/5
[58] Field of Search ............... 260/519, 518 A; 424/5

[56] References Cited

U.S. PATENT DOCUMENTS

| | | | |
|---|---|---|---|
| 2,587,936 | 3/1952 | Wollingford | 424/5 |
| 3,042,715 | 7/1962 | Obendorf et al. | 260/519 |
| 3,389,170 | 6/1968 | Habicht | 260/519 |
| 3,484,481 | 12/1969 | Obendorf et al. | 260/519 |
| 3,803,221 | 4/1974 | Ackerman | 260/518 A |

*Primary Examiner*—James H. Reamer
*Attorney, Agent, or Firm*—Wenderoth, Lind & Ponack

[57] ABSTRACT

N-acyl derivatives of 3-amino-2,4,6-triiodobenzoic acid having the formula

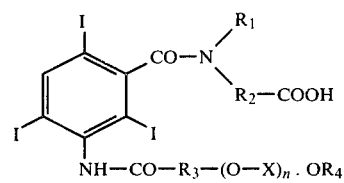

in which $R_1$ is hydrogen, alkyl of up to 4 carbon atoms, alkoxyalkyl of 2-5 carbon atoms or alkoxyalkoxyalkyl of 3-8 carbon atoms, $R_2$ is alkylene of up to 5 carbon atoms, $R_3$ is alkylene of up to 3 carbon atoms, $R_4$ is alkyl of up to 6 carbon atoms, X is straight chain or branched alkylene with two or three carbon atoms in the main chain and n is 0, 1 or 2 and the pharmaceutically acceptable salts thereof, which are useful as X-ray contrast media for intravenous cholecystographie.

8 Claims, No Drawings

N-ACYL DERIVATIVES OF 3-AMINO-2,4,6-TRIIODOBENZOIC ACID

The invention relates to N-acyl derivatives of 3-amino-2,4,6-triiodobenzoic acid which have valuable properties as X-ray constrast media, which make them particularly suitable for use in intravenous cholecystography.

It is essential that, in addition to having a good radioopaque action, an X-ray contrast medium to be administered intravenously is as free as possible from unpleasant side effects, since these can have a particularly aggravating effect in the case of the intravenous method of administration. Furthermore, there is, to an increasing extent, the requirement that X-ray contrast media are rapidly excreted from the human body again so that the danger of retaining iodine-containing substances in the body over a relatively long period is avoided. In this respect, the intravenous X-ray contrast media commercially available hitherto are not yet completely satisfactory, and in addition allergic symptoms appear again and again when iodine-containing compounds are injected into sensitive persons, so that every further intravenous contrast medium which has a good action is an enrichment because it makes it easier to change the formulation in examinations carried out in rapid succession.

A measurement which can be used for good ease of elimination of a compound from the body is the degree of bonding of the substance to protein. The stronger this bonding is, the more a longer retention of the substances in the human body is to be reckoned with. In contrast to this, in the case of X-ray contrast media for demonstrating the gall bladder, the learned opinion hitherto was frequently that only X-ray contrast media with a high protein bonding make a good demonstration of the gall bladder possible.

Commercially available contrast media, which can be administered intravenously, for cholecystography therefore also have a high degree of bonding to protein. Thus, for example, the substance adipic acid bis-(3-carboxy-2,4,6-triiodoanilide), generic name Iodipamide has, in vitro (cattle albumin), a protein bonding of 77–95%, determined according to the method of Witiak et al, Biochemical Pharmacology 18, 971–977, depending on the albumin batch used, and Ioglycamide exhibits a protein bonding of 82%.

However, a lower protein bonding has recently been regarded as an indication of improved tolerance; see Taenzer et al, Fortschr. Röntgenstr. 123, 5, 414–418 (1975).

Amides of 3-amino-2,4,6-triiodobenzoic acid which are acylated in the nuclear amino group by the radical of a lower aliphatic monocarboxylic acid have already been proposed as contrast media for intravenous cholecystography, see U.S. Pat. application of Obendorf et al, Ser. No. 224,264, now U.S. Pat. 3,334,134.

These compounds have a protein bonding of about 40%. They have not been used in practice since their tolerance was not satisfactory.

It has now been found, surprisingly, that N-acyl derivatives of 3-amino-2,4,6-triiodobenzoic acid, which derivatives have the general formula I

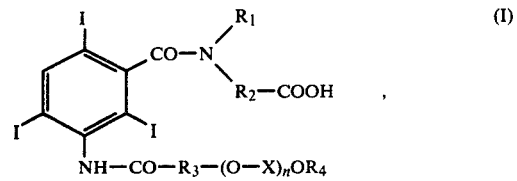

in which $R_1$ is hydrogen, alkyl of up to 4 carbon atoms, alkoxyalkyl of 2–5 C atoms or alkoxyalkoxyalkyl of 3–8 C atoms, $R_2$ is alkylene of up to 5 carbon atoms, $R_3$ is alkylene of up to 3 carbon atoms, $R_4$ is alkyl of up to 6 carbon atoms, X is straight chain or branched alkylene with two or three carbon atoms in the main chain and n is 0, 1 or 2, which thus differ from the compounds of U.S. Pat. No. 3,334,134 by the oxygen content in the chain of the acyl radical, or their pharmaceutically acceptable salts with bases are valuable active compounds for the preparation of contrast media, to be administered intravenously, for cholecystography and cholangiography, which compounds are distinguished by a good rate of excretion within the first 3 hours and a good ease of demonstration of the biliary system, but which have a protein bonding of less than 20%, coupled with low toxicity and good tolerance. It was not to be expected that active compounds with such a low protein bonding could be good biliary contrast media which, in addition, also have the advantage that they can be eliminated from the body particularly rapidly.

Compounds which contain, in the benzoic acid amide grouping, a propionic acid radical or α-methylpropionic acid radical bonded to the amide nitrogen and which, in the nuclear amino group, carry a 7-membered to 12-membered acyl radical which can contain up to 3 ether oxygen atoms, are particularly favourable here. $R_1$ here is preferably hydrogen, an alkyl radical with a maximum of 4 C atoms, an alkoxyalkyl radical with 2–5 C atoms or an alkoxyalkoxyalkyl radical with 3–8 C atoms.

Particularly favourable results are obtained, for example, with N-[3-(3',6',9'-trioxadecanoyl-(1')-amino)-2,4,6-triiodobenzoyl]-β-amino-α-methylpropionic acid, N-[3-(4',7',10'-trioxaundecanoyl-(1')-amino)-2,4,6-triiodobenzoyl]-β-amino-α-methylpropionic acid, N-[3-(4',7'-dioxa-8'-methyl-nonanoyl-(1')-amino)-2,4,6-triiodobenzoyl]-β-amino-α-methylpropionic acid, N-[3-(4',7'-dioxa-5'-methyl-octanoyl-(1')-amino)-2,4,6-triiodobenzoyl]-β-amino-α-methylpropionic acid, N-[3-(4',7'-dioxaoctanoyl-(1')-amino)-2,4,6-triiodobenzoyl]-β-amino-α-methylpropionic acid, N-[3-(4',7',10'-trioxaundecanoyl-(1')-amino)-2,4,6-triiodobenzoyl]-N-ethyl-β-aminopropionic acid and N-[3-(4',7',10'-trioxa-2'-methylundecanoyl-(1')-amino)-2,4,6-triiodobenzoyl]-β-amino-α-methylpropionic acid, in particular in the form of their pharmaceutically acceptable salts.

The process for the manufacture of these compounds is characterised in that derivatives of 3-amino-2,4,6-triiodobenzoic acid, which derivatives have the general formula II

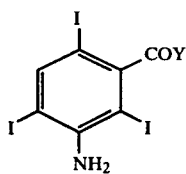

in which Y denotes chlorine or bromine or the group

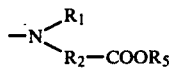

wherein $R_5$ denotes hydrogen or an alkyl radical and $R_1$ and $R_2$ are defined as in formula I, are reacted with acid chlorides of the general formula

in which $R_3$, $R_4$, X and n are defined as in formula I, and halogen atoms which are present in the molecule and bonded to the carboxyl group are converted into the acid amide group by reaction with an amine of the general formula

in which $R_1$, $R_2$ and $R_5$ are defined as above, after which ester groups which are present are saponified and the process products are isolated as free acids or as salts.

The reaction of the derivatives of 3-amino-2,4,6-triiodobenzoic acid with the acid chloride of the formula III is advantageously carried out in an inert solvent, such as, for example, halogenated hydrocarbons, in particular chloroform or carbon tetrachloride, aromatic hydrocarbons, such as, for example, benzene, toluene or chlorobenzene, or strongly polar solvents, such as, for example, acetonitrile. The reaction is preferably carried out at elevated temperature, for example at 60°–150° C., preferably up to 135° C., the procedure appropriately being carried out at the boiling point of the solvent. The addition of a small amount of acid can promote the reaction.

If Y in the starting material of the formula II is chlorine or bromine, the acid halide radical must subsequently be converted into the substituted amide radical. The reaction with the compounds of the formula IV, which is necessary for this, also takes place in a solvent, such as, for example, chloroform, toluene or ether, at elevated temperature. It can also be carried out without a solvent. Appropriately, the medium which was used for the reaction with the compounds of the formula III is retained.

The compounds of the formula I obtained can be isolated as free acids or as salts in the customary manner. The free acids can, of course, also be converted into the pharmaceutically acceptable salts, preferably the sodium, potassium or lithium salts or those with organic bases, in particular the methylglucamine salts and diethanolamine salts, in the customary manner.

The solutions required for intravenous administration are preferably aqueous solutions of the pharmaceutically acceptable salts, which are obtained either by dissolving the salt in water or by neutralising the corresponding acid of the formula I with aqueous solutions of bases leading to these salts. If desired, thickeners can be added.

Because of the steric hindrance existing in the compounds of the formula I, in some cases the occurrence of cis-trans isomerism is possible.

EXAMPLE 1

1 drop of sulphuric acid is added to a solution of 30.7 g of N-[3-amino-2,4,6-triiodobenzoyl]-β-amino-α-methylpropionic acid methyl ester and 11.8 g of 3,6,9-trioxadecanoyl chloride in 150 ml of chloroform and the mixture is boiled under reflux for 7 hours. Some sodium acetate is then added and the mixture is evaporated. The oily evaporation residue is dissolved in 300 ml of methanol, 30 ml of 4N NaOH are added and the mixture is boiled until saponification is complete. It is again evaporated, the residue is dissolved in 400 ml of water and the acid is precipitated with 4N HCl. The acid precipitates as a viscous plastic composition and can be crystallised from ethyl acetate. The yield is 27.8 g of N-[3',6',9'-trioxadecanoyl-(1')-amino-2,4,6-triiodobenzoyl]-β-amino-α-methylpropionic acid, melting point 135°–137° C.

EXAMPLE 2

985 g of N-(3-amino-2,4,6-triiodobenzoyl)-β-amino-α-methylpropionic acid methyl ester are dissolved in 5 l of chloroform, 1 ml of $H_2SO_4$ is added, 370 g of 4,7,10-trioxaundecanoyl chloride is added dropwise in the course of 2 hours, whilst boiling under reflux, and the mixture is then boiled for a further 12 hours. In order to bring the reaction to completion, a further 105 g of 3,7,10-trioxaundecanoyl chloride are added dropwise, in the course of 2 hours, and the mixture is boiled for a further 4 hours. The reaction solution is evaporated and the dark oily evaporation residue is dissolved in 2 l of methanol and saponified by adding 400 g of 40% strength NaOH and boiling for 10 minutes. The solvent is distilled off again, the residue is taken up in 5 l of water and the solution is clarified by filtration and acidified with HCl. The oily acid obtained is extracted by washing with chloroform and the chloroform phase is dried over $Na_2SO_4$ and evaporated. The evaporation residue is crystallised from a mixture of 1 l of methanol and 1 l of ethyl acetate. 968 g of N-[3-(4',7',10'-trioxaundecanoyl-(1')-amino)-2,4,6-triiodobenzoyl]-β-amino-α-methylpropionic acid, melting point=155°–160° C., are obtained as primary crystals, and after concentrating the mixture to 600 ml a further 122 g are obtained.

7.74 g of the N-[3-(4',7',10'-trioxaundecanoyl-(1')-amino)-2,4,6-triiodobenzoyl]-β-amino-α-methylpropionic acid thus obtained and 1.95 g of N-methylglucamine are dissolved in 40 ml of methanol and the clear solution is evaporated in the cold, in vacuo, to give a foamed resin. The N-methylglucamine salt of N-[3-(4',7',10'-trioxaundecanoyl-(1')-amino-2,4,6-triiodobenzoyl]-β-amino-α-methylpropionic acid, which is readily soluble in water, is obtained in quantitative yield. The salt obtained is hygroscopic and melts at 35°–42° C.

EXAMPLE 3

28.4 g of 4,7,10-trioxaundecanoyl chloride and 1 drop of $H_2SO_4$ are added to a solution of 29.2 g of N-(3-amino-2,4,6-triiodobenzoyl)-aminoacetic acid ethyl ester in 100 ml of chloroform and the mixture is boiled under reflux for 10 hours. After adding some sodium acetate, the mixture is clarified by filtration and evaporated, the residue is dissolved in 300 ml of methanol, 30 ml of 4N NaOH are added and saponification is effected by boiling. The methanol is distilled off again, the residue is dissolved in 400 ml of water and the product is precipitated with HCl. The oily precipitate can be crystallised from ethyl acetate; the yield is 14.6 g of N-[3-(4′,7′,10′-trioxaundecanoyl-(1′)-amino)-2,4,6-triiodobenzoyl]-aminoacetic acid, melting point = 198°–200° C.

EXAMPLE 4

370 g of N-(3-amino-2,4,6-triiodobenzoyl)-3-amino-α-methylpropionic acid methyl ester are dissolved in 1 l of toluene, 135 g of 4,7-dioxa-8-methyl-nonanoyl chloride are added and the mixture is boiled under reflux for 7 hours. The precipitate which forms on standing overnight and which is difficult to filter off is dissolved by adding methanol, the solution is then evaporated and the residue is saponified in methanolic-aqueous NaOH. The desired compound is precipitated from aqueous phase with HCl and the plastic product thereby obtained is crystallised from ethyl acetate. A total of 358 g of N-[3-(4′,7′-dioxa-8′-methylnonanoyl-(1′)-2,4,6-triiodobenzoyl]-β-amino-α-methylpropionic acid, melting point = 180°–185° C., are obtained; 246 g are obtained as primary crystals, 85 g are obtained from the mother liquor and thereafter a further 27 g are obtained.

EXAMPLE 5

53.3 g of 3-amino-2,4,6-triiodobenzoyl chloride are dissolved in 300 ml of chloroform, 25.2 g of 4,7,10-trioxaundecanoyl chloride and 1 drop of $H_2SO_4$ are added and the mixture is boiled under reflux for 6 hours. After cooling, the reaction mix is poured onto ice-water and the chloroform phase is washed with cold, dilute NaOH and ice-water, dried over $Na_2SO_4$ and evaporated. 53.8 g of 3-(4′,7′,10′-trioxaundecanoyl-(1′)-2,4,6-triiodobenzoyl chloride of a honey-like consistency are obtained.

26.9 g of the product obtained are dissolved in 50 ml of chloroform, 17.4 g of N-isopropyl-β-aminopropionic acid methyl ester are added and the mixture is boiled under reflux for 1 hour. After cooling, the mixture is washed with dilute HCl, NaHCO$_3$ solution and water, dried over NaCl and evaporated. The evaporation residue is saponified in methanolic-aqueous NaOH and the desired compound is precipitated as a sticky mass from aqueous solution, using HCl.

14.6 g of N-3-(4′,7′,10′-trioxaundecanoyl-(1′)-amino)-2,4,6-triiodobenzoyl]-N-isopropyl-β-amino-propionic acid, melting point = 165°–168° C., are obtained by crystallisation from ethyl acetate.

EXAMPLE 6

43.6 g of 3-(4′,7′,10′-trioxaundecanoyl-(1′)-amino)-2,4,6-triiodobenzoyl chloride obtained according to Example 5 are dissolved in 250 ml of chloroform and reacted with 35 g of N-(3-methoxypropyl)-β-aminopropionic acid methyl ester. After boiling under reflux for 1½ hours, the solution is washed with dilute HCl, KHCO$_3$ solution and water, dried over NaCl and evaporated. The evaporation residue, that is to say 53.1 g of an oil, is the methyl ester of the desired compound. The acid is obtained as a viscous oil by saponification of the methyl ester in aqueous-methanolic NaOH and precipitation from the aqueous solution by means of hydrochloric acid.

11.4 g of this acid are dissolved in about 30 ml of methanol, the pH is adjusted to 7.8 by adding dilute NaOH and the mixture is clarified by filtration. The filtrate is evaporated, the residue is dissolved again in pure methanol and the solution is evaporated in vacuo to give a foamed resin. 10.4 g of sodium N-[3-(4′,7′,10′-trioxyaundecanoyl-(1′)-amino)-2,4,6-triiodobenzoyl]-N-(3″-methoxypropyl)-β-aminopropionate, melting point = 105°–115° C., are obtained.

The same compound is obtained by reacting N-(3-amino-2,4,6-triiodobenzoyl)-N-(3′-methoxypropyl)-β-aminopropionic acid methyl ester in chlorobenzene with 4,7,10-trioxaundecanoyl chloride in the presence of some $H_2SO_4$, subsequently saponifying the product and preparing the Na salt. The following compounds are obtained in an analogous manner to the preceding examples: N-[3-(2′-methoxypropionylamino)-2,4,6-triiodobenzoyl]-β-amino-α-methylpropionic acid, melting point = 230°–232° C., N-[3-(3′,6′-dioxa-heptanoyl-(1′)-amino)-2,4,6-triiodobenzoyl]-β-amino-α-methylpropionic acid, melting point = 105°–110° C., N-[3-(4′,7′-dioxa-octanoyl-(1′)-amino)-2,4,6-triiodobenzoyl]-β-amino-α-methylpropionic acid, melting point = 186°–189° C., N-[3-(4′,7′-dioxa-5′-methyl-octanoyl-(1′)-amino)-2,4,6-triiodobenzoyl]-β-amino-α-methylpropionic acid, melting point = 187°–188° C., N-[3-(4′,7′,10′-trioxaundecanoyl-(1′)-amino)-2,4,6-triiodobenzoyl]-β-amino-propionic acid, melting point = 155°–162° C., N-[3-(4′,7′,10′-trioxaundecanoyl-(1′)-amino)-2,4,6-triiodobenzoyl]-N-methyl-β-amino-propionic acid, melting point = 64°–75° C. (amorphous), N-[3-(4′,7′,10′-trioxaundecanoyl-(1′)-amino)-2,4,6-triiodobenzoyl]-N-ethyl-β-amino-propionic acid, melting point = 131°–134° C., sodium N-[3-(4′,7′,10′-trioxaundecanoyl-(1′)-amino)-2,4,6-triiodobenzoyl]-N-(3″-methoxypropyl)-β-amino-propionate, melting point = 105°–115° C. amorphous), N-[3-(4′,7′,10′-trioxaundecanoyl-(1′)-2,4,6-triiodobenzoyl]-β-amino-butyric acid, melting point = 150°–154° C., N-[3-(4′,7′,10′-trioxadodecanoyl-(1′)-amino)-2,4,6-triiodobenzoyl]-β-amino-α-methyl-propionic acid, melting point = 175°–177° C., N-[3-(4′,7′,10′-trioxatetradecanoyl-(1′)-amino)-2,4,6-triiodobenzoyl]-β-amino-α-methylpropionic acid, melting point = 178°–180° C., N-[3-(4′,7′,10′-trioxa-2′-methyl-undecanoyl-(1′)-amino)-2,4,6-triiodobenzoyl]-β-amino-α-methylpropionic acid, melting point = 173°–175° C. and the Na salt of N-[3-(4′,7′-dioxaoctanoyl-(1′)-amino)-2,4,6-triiodobenzoyl]-N-(3″,6″-dioxaheptyl)-β-aminopropionic acid, hygroscopic mass, obtained by evaporating a solution.

The injection solutions are appropriately prepared by dissolving the corresponding carboxylic acids in aqueous solutions of pharmaceutically suitable bases and adjusting the solutions to a desired concentration. A solution of a particular concentration can also be prepared by dissolving a suitable salt of a compound. Appropriate additives can be used to improve the properties.

EXAMPLE 7

500.0 g of N-[3-(4′,7′,10′-trioxaundecanoyl-(1′)-amino)-2,4,6-triiodobenzoyl]-β-amino-α-methylpropionic acid are dissolved in 646 ml of 1N NaOH, 20.0 g of polyvinylpyrrolidone are then dissolved and the solution is diluted to a volume of 2.0 l.

EXAMPLE 8

760.1 g of N-[3-(3′,6′,9′-trioxadecanoyl-(1′)-amino)-2,4,6-triiodobenzoyl]-β-amino-α-methylpropionic acid are dissolved in 1.0 l of a 1N aqueous N-methyl-d-glucosamine solution and the solution is then diluted to 1,900 ml. The solution contains 40.0 g of the compound employed, per 100 ml.

What we claim is:

1. A compound selected from the group consisting of compounds of the formula

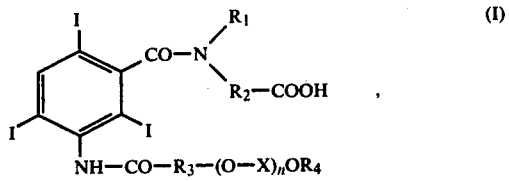

in which $R_1$ is hydrogen, alkyl of up to 4 carbon atoms, alkoxyalkyl of 2–5 C atoms or alkoxyalkoxyalkyl of 3–8 C atoms, $R_2$ is alkylene of up to 5 carbon atoms, $R_3$ is alkylene of up to 3 carbon atoms, $R_4$ is alkyl of up to 6 carbon atoms, X is straight chain or branched alkylene with two or three carbon atoms in the main chain and n is 0, 1 or 2 and the pharmaceutically acceptable salts thereof with bases.

2. A compound according to claim 1, selected from the group consisting of N-[3-(3',6',9'-trioxadecanoyl-(1')-amino)-2,4,6-triiodobenzoyl]-β-amino-α-methylpropionic acid, and the pharmaceutically acceptable salts thereof.

3. A compound according to claim 1, selected from the group consisting of N-[3-(4',7',10'-trioxaundecanoyl-(1')-amino)-2,4,6-triiodobenzoyl]-β-amino-α-methylpropionic acid, and the pharmaceutically acceptable salts thereof.

4. A compound according to claim 1, selected from the group consisting of N-[3-(4',7'-dioxa-8'-methylnonanoyl-(1')-amino)-2,4,6-triiodobenzoyl]-β-amino-α-methylpropionic acid, and the pharmaceutically acceptable salts thereof.

5. A compound according to claim 1, selected from the group consisting of N-[3-(4',7'-dioxa-5'-methyloctanoyl-(1')-amino)-2,4,6-triiodobenzoyl]-β-amino-α-methylpropionic acid, and the pharmaceutically acceptable salts thereof.

6. A compound according to claim 1, selected from the group consisting of N-[3-(4',7',10'-trioxa-2'-methylundecanoyl-(1')-amino)-2,4,6-triiodobenzoyl]-β-amino-α-methylpropionic acid, and the pharmaceutically acceptable salts thereof.

7. A compound according to claim 1, selected from the group consisting of N-[3-(4',7'-dioxa-octanoyl-(1')-amino)-2,4,6-triiodobenzoyl]-β-amino-α-methylpropionic acid, and the pharmaceutically acceptable salts thereof.

8. A compound according to claim 1, selected from the group consisting of N-[3-(4',7',10'-trioxaundecanoyl-(1')-amino)-2,4,6-triiodobenzoyl]-N-ethyl-β-aminopropionic acid, and the pharmceutically acceptable salts thereof.